(12) United States Patent
Eskuri (10) Patent No.: US 7,785,273 B2
(45) Date of Patent: Aug. 31, 2010

(54) GUIDEWIRE WITH REINFORCING MEMBER

(75) Inventor: Alan Eskuri, Hanover, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1058 days.

(21) Appl. No.: 10/667,043

(22) Filed: Sep. 22, 2003

(65) Prior Publication Data

US 2005/0065456 A1    Mar. 24, 2005

(51) Int. Cl.
*A61B 5/00*    (2006.01)
*A61M 25/00*    (2006.01)

(52) U.S. Cl. ....................................................... 600/585
(58) Field of Classification Search ......... 600/433–435, 600/585
See application file for complete search history.

(56) References Cited

U.S. PATENT DOCUMENTS

| 3,174,851 A | 3/1965 | Buehler et al. |
| 3,351,463 A | 11/1967 | Rozner et al. |
| 3,753,700 A | 8/1973 | Harrison et al. |
| 4,080,706 A | 3/1978 | Heilman et al. |
| 4,456,017 A | 6/1984 | Miles |
| 4,538,622 A | 9/1985 | Samson et al. |
| 4,748,986 A | 6/1988 | Morrison et al. |
| 4,763,647 A | 8/1988 | Gambale |
| 4,813,434 A | 3/1989 | Buchbinder et al. |
| 4,846,186 A | 7/1989 | Box et al. |
| 4,884,579 A | 12/1989 | Engelson |
| 4,925,445 A | 5/1990 | Sakamoto et al. |
| 4,984,581 A | 1/1991 | Stice |
| 5,025,799 A | 6/1991 | Wilson |
| 5,069,226 A | 12/1991 | Yamauchi et al. |
| 5,095,915 A | 3/1992 | Engelson |
| 5,102,403 A | 4/1992 | Alt |
| 5,109,867 A | 5/1992 | Twyford, Jr. |
| 5,111,829 A | 5/1992 | Alvarez de Toledo |
| 5,133,364 A | 7/1992 | Palermo et al. |
| 5,154,705 A | 10/1992 | Fleischhacker et al. |
| 5,165,421 A | 11/1992 | Fleischhacker et al. |
| 5,213,111 A | 5/1993 | Cook et al. |

(Continued)

FOREIGN PATENT DOCUMENTS

EP    0 274 412 A2    7/1988

(Continued)

OTHER PUBLICATIONS

U.S. Appl. No. 10/261,019 to Reynolds et al., filed Sep. 20, 2002.

(Continued)

*Primary Examiner*—Max Hindenburg
*Assistant Examiner*—H. Q. Nguyen
(74) *Attorney, Agent, or Firm*—Crompton, Seager & Tufte, LLC (57) ABSTRACT

Some disclosed embodiments pertain to a guidewire having a stainless steel elongated core member. A nickel-titanium reinforcing member may be located about a distal region of the core member having a reduced diameter, wherein a portion of the distal region of the core member extends beyond the reinforcing member. The nickel-titanium member may have added physical characteristics providing superior flexibility. An outer member may be placed about the distal portion of the core wire and extend over the reinforcing member.

20 Claims, 11 Drawing Sheets

U.S. PATENT DOCUMENTS

| | | | |
|---|---|---|---|
| 5,230,348 A | 7/1993 | Ishibe et al. | |
| 5,238,004 A | 8/1993 | Sahatjian et al. | |
| 5,242,759 A | 9/1993 | Hall | |
| 5,253,653 A | 10/1993 | Daigle et al. | |
| RE34,466 E | 12/1993 | Taylor et al. | |
| 5,273,052 A | 12/1993 | Kraus et al. | |
| 5,275,173 A | 1/1994 | Samson et al. | |
| 5,312,356 A | 5/1994 | Engelson et al. | |
| 5,333,620 A | 8/1994 | Moutafis et al. | |
| 5,341,818 A | 8/1994 | Abrams et al. | |
| 5,345,945 A | 9/1994 | Hodgson et al. | |
| 5,358,796 A | 10/1994 | Nakamura et al. | |
| 5,365,942 A | 11/1994 | Shank | |
| 5,365,943 A | 11/1994 | Jansen | |
| 5,368,661 A | 11/1994 | Nakamura et al. | |
| 5,402,799 A | 4/1995 | Colon et al. | |
| 5,409,015 A | 4/1995 | Palermo | |
| 5,411,476 A | 5/1995 | Abrams et al. | |
| 5,415,633 A | 5/1995 | Lazarus et al. | |
| 5,421,349 A | 6/1995 | Rodriguez et al. | |
| 5,429,139 A | 7/1995 | Sauter | |
| 5,433,200 A | 7/1995 | Fleischhacker, Jr. | |
| 5,437,288 A | 8/1995 | Schwartz et al. | |
| 5,452,726 A | 9/1995 | Burmeister et al. | |
| 5,488,959 A | 2/1996 | Ales | |
| 5,497,785 A | 3/1996 | Viera | |
| 5,507,301 A | 4/1996 | Wasicek et al. | |
| 5,520,194 A | 5/1996 | Miyata et al. | |
| 5,551,444 A | 9/1996 | Finlayson | |
| 5,573,520 A | 11/1996 | Schwartz et al. | |
| 5,596,996 A * | 1/1997 | Johanson et al. | 600/585 |
| 5,599,492 A | 2/1997 | Engelson | |
| 5,636,642 A | 6/1997 | Palermo | |
| 5,637,089 A | 6/1997 | Abrams et al. | |
| 5,640,970 A * | 6/1997 | Arenas | 600/585 |
| 5,651,373 A | 7/1997 | Mah | |
| 5,664,580 A | 9/1997 | Erickson et al. | |
| 5,666,969 A | 9/1997 | Urick et al. | |
| 5,695,111 A | 12/1997 | Nanis et al. | |
| 5,697,380 A * | 12/1997 | Quiachon et al. | 600/585 |
| 5,720,300 A | 2/1998 | Fagan et al. | |
| 5,724,989 A | 3/1998 | Dobson | |
| 5,749,837 A | 5/1998 | Palermo et al. | |
| 5,769,796 A | 6/1998 | Palermo et al. | |
| 5,772,609 A | 6/1998 | Nguyen et al. | |
| 5,772,641 A | 6/1998 | Wilson | |
| 5,782,741 A | 7/1998 | Bradshaw et al. | |
| 5,782,776 A | 7/1998 | Hani | |
| 5,797,857 A | 8/1998 | Obitsu | |
| 5,813,997 A | 9/1998 | Imran et al. | |
| 5,820,571 A | 10/1998 | Erades et al. | |
| 5,833,631 A | 11/1998 | Nguyen | |
| 5,836,893 A | 11/1998 | Urick | |
| 5,865,768 A | 2/1999 | Orr | |
| 5,876,356 A | 3/1999 | Viera et al. | |
| 5,891,055 A | 4/1999 | Sauter | |
| 5,902,254 A | 5/1999 | Magram | |
| 5,916,166 A | 6/1999 | Reiss et al. | |
| 5,916,178 A * | 6/1999 | Noone et al. | 600/585 |
| 5,951,496 A | 9/1999 | Willi | |
| 5,954,672 A | 9/1999 | Schwager | |
| 5,957,903 A | 9/1999 | Mirzaee et al. | |
| 5,980,471 A | 11/1999 | Jafari | |
| 6,001,068 A | 12/1999 | Uchino et al. | |
| 6,106,488 A | 8/2000 | Fleming et al. | |
| 6,132,388 A | 10/2000 | Fleming et al. | |
| 6,139,510 A | 10/2000 | Palermo | |
| 6,165,292 A | 12/2000 | Abrams et al. | |
| 6,183,420 B1 | 2/2001 | Douk et al. | |
| 6,203,505 B1 | 3/2001 | Jalisi et al. | |
| RE37,148 E | 4/2001 | Shank | |
| 6,210,395 B1 | 4/2001 | Fleischhacker et al. | |
| 6,234,981 B1 | 5/2001 | Howland | |
| 6,245,030 B1 | 6/2001 | DuBois et al. | |
| 6,248,082 B1 | 6/2001 | Jafari | |
| 6,251,085 B1 | 6/2001 | Tezuka | |
| 6,306,105 B1 | 10/2001 | Rooney et al. | |
| 6,352,515 B1 | 3/2002 | Anderson et al. | |
| 6,387,060 B1 | 5/2002 | Jalisi | |
| 6,410,886 B1 | 6/2002 | Julien | |
| 6,428,489 B1 | 8/2002 | Jacobsen et al. | |
| 6,488,637 B1 | 12/2002 | Eder et al. | |
| 6,508,803 B1 | 1/2003 | Horikawa et al. | |
| 6,620,114 B2 * | 9/2003 | Vrba et al. | 600/585 |
| 6,887,235 B2 * | 5/2005 | O'Connor et al. | 606/27 |
| 7,074,197 B2 * | 7/2006 | Reynolds et al. | 600/585 |
| 7,182,735 B2 * | 2/2007 | Shireman et al. | 600/585 |
| 2002/0013540 A1 | 1/2002 | Jacobsen et al. | |
| 2002/0042582 A1 * | 4/2002 | Vrba et al. | 600/585 |
| 2002/0183654 A1 * | 12/2002 | Zhou | 600/585 |
| 2003/0069520 A1 | 4/2003 | Skujins et al. | |
| 2003/0069521 A1 | 4/2003 | Reynolds et al. | |
| 2003/0181828 A1 * | 9/2003 | Fujimoto et al. | 600/585 |
| 2004/0064069 A1 * | 4/2004 | Reynolds et al. | 600/585 |
| 2004/0122340 A1 * | 6/2004 | Vrba et al. | 600/585 |
| 2005/0038359 A1 * | 2/2005 | Aimi et al. | 600/585 |
| 2005/0054952 A1 * | 3/2005 | Eskuri et al. | 600/585 |

FOREIGN PATENT DOCUMENTS

| | | |
|---|---|---|
| EP | 0 386 921 A2 | 9/1990 |
| EP | 0 491 349 A2 | 6/1992 |
| EP | 0 806 220 A2 | 11/1997 |
| EP | 0 838 230 A2 | 4/1998 |
| WO | WO 00/40286 A1 | 7/2000 |

OTHER PUBLICATIONS

U.S. Appl. No. 10/346,698 to Miller et al., filed Jan. 17, 2003.
U.S. Appl. No. 10/375,766 to Reynolds et al., filed Feb. 26, 2003.
U.S. Appl. No. 10/376,068 to Shireman et al., filed Feb. 26, 2003.

* cited by examiner

GUIDEWIRE WITH REINFORCING MEMBER

FIELD OF THE INVENTION

The invention generally pertains to guidewires, and more particularly to guidewires including a reinforcing member including a nickel-titanium alloy. More particularly the invention pertains to guidewires having a stainless steel core and a reinforcing member including a nickel-titanium alloy located in a distal region.

BACKGROUND OF THE INVENTION

A wide variety of guidewires have been developed for medical use, for example intravascular use. Intravascular guidewires are commonly used in conjunction with intravascular devices such as catheters to facilitate navigation through the vasculature of a patient. Because the vasculature of a patient may be very tortuous, it is desirable to combine a number of performance features in a guidewire. For example, it is sometimes desirable that the guidewire have a relatively high level of pushability and torqueability, particularly near its proximal end. It is also sometimes desirable that a device be relatively flexible, particularly near its distal end. A number of different guidewire structures and assemblies are known, each having certain advantages and disadvantages. However, there is an ongoing need to provide alternative guidewire structures and assemblies.

SUMMARY OF THE INVENTION

The invention provides several alternative designs, materials and combinations in a guidewire with improved characteristics.

One embodiment includes a guidewire having an elongated core member with a reinforcing member disposed about a portion of the distal region of the core member. A distal portion of the core member extends beyond the reinforcing member. An outer member is positioned over the distal portion of the core member and extends over at least a portion of the reinforcing member.

Another embodiment provides a guidewire including an elongated core member, wherein at least a portion of the distal region of the core member includes stainless steel. A reinforcing member preferably formed of a nickel-titanium alloy is disposed about a portion of the distal region of the core member, wherein the distal end of the reinforcing member terminates proximal of a distal portion of the distal region of the core member. An outer member is positioned over at least a portion of the reinforcing member and the portion of the core member distal of the reinforcing member.

Another embodiment provides a guidewire configured for use in a patient's body, the guidewire having an elongated inner core member including stainless steel. The core member includes at least a proximal portion having a first cross-sectional area, an intermediate portion having a second cross-sectional area, and a distal portion having a ribbon profile. Preferably, the first cross-sectional area is larger than the second cross-sectional area, which is larger than the ribbon profile.

An elongated reinforcing member is disposed about the intermediate portion of the core member. The reinforcing member preferably includes a nickel-titanium alloy. The reinforcing member may be a coil, tubular member or at least one ribbon wire helically wrapped about the core member. The reinforcing member is preferably of a different material than the intermediate portion of the core member. Therefore, providing characteristics not otherwise present in the reinforced portion.

A spring tip, preferably including stainless steel, is positioned about the distal portion of the core member and extends over the reinforcing member. The spring tip preferably has an outside diameter substantially equal to the diameter of the proximal portion of the core member adjacent the spring tip. Substantially equivalent diameters in this region provide for a smooth transition along the guidewire that enables medical devices to more easily pass along the guidewire during a medical procedure.

The above summary of some embodiments is not intended to describe each disclosed embodiment or every implementation of the present invention. The Figures, and Detailed Description which follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF THE PREFERRED EMBODIMENTS

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

Weight percent, percent by weight, wt %, wt-%, % by weight, and the like are synonyms that refer to the concentration of a substance as the weight of that substance divided by the weight of the composition and multiplied by 100.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

Figure 1:
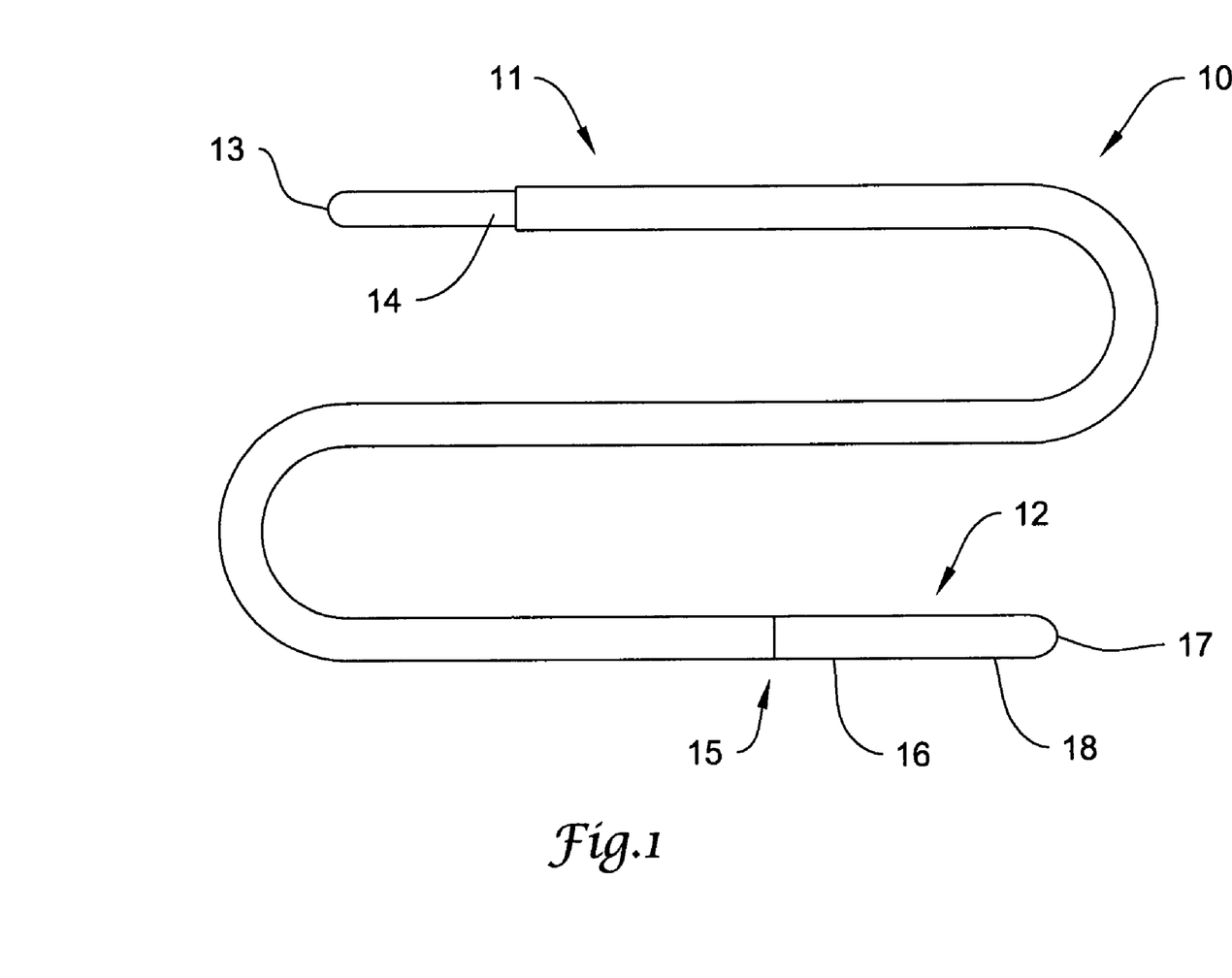
FIG. 1 is a schematic plan view of a guidewire generally.

Refer now to FIG. 1, which is a schematic plan view of one example embodiment of a guidewire 10. The guidewire 10 includes a proximal section 11 defining a proximal end 13, and a distal section 15 defining a distal end 17. A distal tip 12 is located near distal end 17.

It can be seen that guidewire 10 may include a core member or wire 14. The distal section 15 includes a proximal portion 16 and a distal portion 18. Core wire 14 can be made of any suitable materials including metals, metal alloys, polymers, or the like, or combinations or mixtures thereof. Some examples of suitable metals and metal alloys include stainless steel, such as 304v stainless steel; nickel-titanium alloy, such as linear elastic or superelastic (i.e., pseudo elastic) nitinol, nickel-chromium alloy, nickel-chromium-iron alloy, cobalt alloy, tungsten, tungsten alloy, Elgiloy, MP35N, or the like; or other suitable materials.

The word nitinol was coined by a group of researchers at the United States Naval Ordinance Laboratory (NOL) who were the first to observe the shape memory behavior of this material. The word nitinol is an acronym including the chemical symbol for nickel (Ni), the chemical symbol for titanium (Ti), and an acronym identifying the Naval Ordinance Laboratory (NOL). In some embodiments, nitinol alloys can include in the range of about 50 to about 60 weight percent nickel, with the remainder being essentially titanium. It should be understood, however, that in other embodiments, the range of weight percent nickel and titanium, and/or other trace elements may vary from these ranges. Within the family of commercially available nitinol alloys are categories designated as "superelastic" (i.e., pseudo elastic) and "linear elastic" which, although similar in chemistry, exhibit distinct and useful mechanical properties.

In some embodiments, a superelastic alloy, for example a superelastic Nitinol, can be used to achieve desired properties. Such alloys typically display a substantial "superelastic plateau" or "flag region" in its stress/strain curve. Such alloys can be desirable in some embodiments because a suitable superelastic alloy will provide a reinforcing member that exhibits some enhanced ability, relative to some other non-superelastic materials, of substantially recovering its shape without significant plastic deformation, upon the application and release of stress, for example, during placement of the catheter in the body.

In some other embodiments, a linear elastic alloy, for example a linear elastic Nitinol, can be used to achieve desired properties. For example, in some embodiments, certain linear elastic nitinol alloys can be generated by the application of cold work, directional stress and heat treatment such that the material fabricated does not display a substantial "superelastic plateau" or "flag region" in its stress/strain curve. Instead, in such embodiments, as recoverable strain increases, the stress continues to increase in a somewhat linear relationship until plastic deformation begins. In some embodiments, the linear elastic nickel-titanium alloy is an alloy that does not show any martensite/austenite phase changes that are detectable by DSC and DMTA analysis over a large temperature range. For example, in some embodiments, there are no martensite/austenite phase changes detectable by DSC and DMTA analysis in the range of about −60° C. to about 120° C. The mechanical bending properties of such material are, therefore, generally inert to the effect of temperature over a broad range of temperature. In some particular embodiments, the mechanical properties of the alloy at ambient or room temperature are substantially the same as the mechanical properties at body temperature. In some embodiments, the use of the linear elastic nickel-titanium alloy allows the reinforcing member to exhibit superior "pushability" around tortuous anatomy. One example of a suitable nickel-titanium alloy exhibiting at least some linear elastic properties is FHP-NT alloy commercially available from Furukawa Techno Material Co. of Kanagawa, Japan. Additionally, some examples of suitable nickel-titanium alloy exhibiting at least some linear elastic properties include those disclosed in U.S. Pat. Nos. 5,238,004 and 6,508,803, which are incorporated herein by reference.

In at least some embodiments, portions or all of core wire 14 may also be doped with, made of or otherwise include a radiopaque material. Radiopaque materials are understood to be materials capable of producing a relatively bright image on a fluoroscopy screen or another imaging technique during a medical procedure. This relatively bright image aids the user of device 10 in determining its location. Some examples of radiopaque materials can include, but are not limited to, gold, platinum, palladium, tantalum, tungsten alloy, polymer material loaded with a radiopaque filler, and the like. In some embodiments, it is also contemplated that a separate radiopaque member or a series of radiopaque members, such as radiopaque coils, bands, tubes, or other such structures could be attached to the guidewire core wire or incorporated into the core wire by plating, drawing, forging, or ion implantation techniques, and the like.

In some embodiments, a degree of MRI compatibility is imparted into guidewire 10. For example, to enhance compatibility with Magnetic Resonance Imaging (MRI) machines, it may be desirable to make core wire 14, or other portions of the medical device 10, in a manner that would impart a degree of MRI compatibility. For example, core wire 14, or portions thereof, may be made of a material that does not substantially distort the image and create substantial artifacts (artifacts are gaps in the image). Certain ferromagnetic materials, for example, may not be suitable because they may create artifacts in an MRI image. Core wire 14, or portions thereof, may also be made from a material that the MRI machine can image. Some materials that exhibit these characteristics include, for example, tungsten, Elgiloy, MP35N, nitinol, and the like, and others.

The entire core wire 14 can be made of the same material, or in some embodiments, can include portions or sections made of different materials. In some embodiments, the material used to construct core wire 14 is chosen to impart varying flexibility and stiffness characteristics to different portions of core wire 14. For example, proximal section 11 and distal section 15 may be formed of different materials, for example materials having different moduli of elasticity, resulting in a difference in flexibility. In some embodiments, the material used to construct proximal section 11 can be relatively stiff for pushability and torqueability, and the material used to construct distal section 15 can be relatively flexible by comparison for better lateral trackability and steerability. For example, proximal section 11 can be formed of straightened 304v stainless steel wire or ribbon, and distal section 15 can be formed of a straightened super elastic or linear elastic alloy, for example a nickel-titanium alloy wire or ribbon.

In embodiments where different portions of core wire 14 are made of different material, the different portions can be connected using any suitable connecting techniques. For example, the different portions of the core wire can be connected using welding, soldering, brazing, adhesives, or the like, or combinations thereof. Additionally, some embodiments can include one or more mechanical connectors or connector assemblies to connect the different portions of the core wire that are made of different materials. The connector may include any structure generally suitable for connecting portions of a guidewire. One example of a suitable structure includes a structure such as a hypotube or a coiled wire which has an inside diameter sized appropriately to receive and connect to the ends of the proximal portion and the distal portion. Some other examples of suitable techniques and structures that can be used to interconnect different shaft sections are disclosed in U.S. Patent Publication Nos. 2003-0069521 and 2003-0069520, which are incorporated herein by reference.

The length of core member 14 (and/or device 10), or the length of individual portions thereof, is typically dictated by the length and flexibility characteristics desired in the final medical device. For example, proximal section 11 may have a length in the range of about 20 to about 300 centimeters or more and distal section 15 may have a length in the range of about 3 to about 50 centimeters or more. It can be appreciated that alterations in the length of sections 11/15 can be made without departing from the spirit of the invention.

Figure 2:
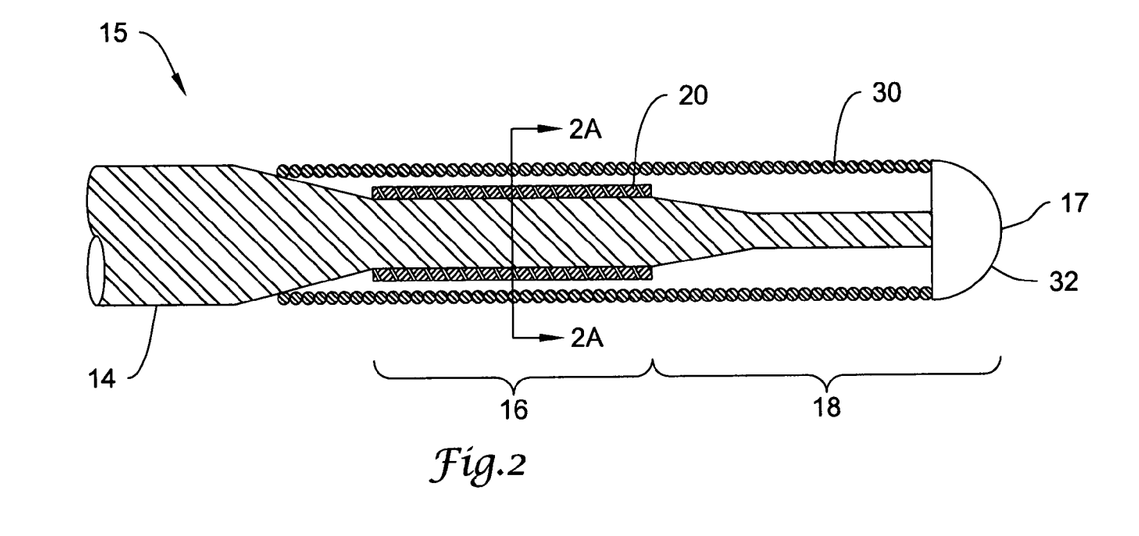
FIG. 2 is a partial cross-sectional view of the distal portion of a guidewire in accordance with the invention.

Core wire 14 can have a solid cross-section, but in some embodiments, can have a hollow cross-section. In yet other embodiments, core wire 14 can include a combination of areas having solid cross-sections and hollow cross-sections. Moreover, core wire 14, or portions thereof, can be made of rounded wire, flattened ribbon, or other such structures having various cross-sectional geometries. The cross-sectional geometries along the length of shaft 14 can be constant or can vary. For example, FIG. 2 depicts core wire 14 as having a round cross-sectional shape. It can be appreciated that other cross-sectional shapes or combinations of shapes may be utilized without departing from the spirit of the invention. For example, the cross-sectional shape of core wire 14 may be oval, rectangular, square, polygonal, and the like, or any suitable shape.

As shown in FIG. 2, distal section 15 may include one or more tapers or tapered regions. In some embodiments distal region 18 may be tapered and have an initial outside size or diameter that can be substantially the same as the outside diameter of proximal section 11, which then tapers to a reduced size or diameter. For example, in some embodiments, distal section 15 can have an initial outside diameter that is in the range of about 0.010 inches to about 0.040 inches that tapers to a diameter in the range of about 0.001 inches to about 0.005 inches. The tapered regions may be linearly tapered, tapered in a curvilinear fashion, uniformly tapered, non-uniformly tapered, or tapered in a step-wise fashion. The angle of any such tapers can vary, depending upon the desired flexibility characteristics. The length of the taper may be selected to obtain a more (longer length) or less (shorter length) gradual transition in stiffness. Although FIG. 2 depicts distal section 15 of core wire 14 as being tapered, it can be appreciated that essentially any portion of core wire 14 may be tapered and the taper can be in either the proximal or the distal direction. As shown in FIG. 2, the tapered region may include one or more portions where the outside diameter is narrowing, for example the tapered portions, and portions where the outside diameter remains essentially constant, for example constant diameter portions. The number, arrangement, size, and length of the narrowing and constant diameter portions can be varied to achieve the desired characteristics, such as flexibility and torque transmission characteristics. The narrowing and constant diameter portions as shown in FIG. 2 are not intended to be limiting, and alterations of this arrangement can be made without departing from the spirit of the invention.

The tapered and constant diameter portions of the tapered region may be formed by any one of a number of different techniques, for example, by centerless grinding methods, stamping methods, and the like. The centerless grinding technique may utilize an indexing system employing sensors (e.g., optical/reflective, magnetic) to avoid excessive grinding of the connection. In addition, the centerless grinding technique may utilize a CBN or diamond abrasive grinding wheel that is well shaped and dressed to avoid grabbing the core wire during the grinding process. In some embodiments, core wire 14 can be centerless ground using a Royal Master HI-AC centerless grinder. Some examples of suitable grinding methods are disclosed in U.S. patent application Ser. No. 10/346, 698 filed Jan. 17, 2003, which is herein incorporated by reference.

As shown in FIG. 2, a reinforcing member 20 may be disposed about a proximal portion 16 of the distal section 15 of the core wire 14. A distal portion 18 of the distal section 15 extends distally beyond the reinforcing member 20. The reinforcing member may be a tubular segment 20 formed of a variety of materials including metals, metal alloys, polymers, and the like. Some examples of material for use in the tubular segment 20 include stainless steel, nickel-titanium alloy, nickel-chromium alloy, nickel-chromium-iron alloy, cobalt alloy, or other suitable materials. In a preferred embodiment, the tubular segment 20 includes nickel-titanium alloy for its superior characteristics such as pushability, with a preferred embodiment further utilizing a stainless steel as a core member 14.

Figure 3A:
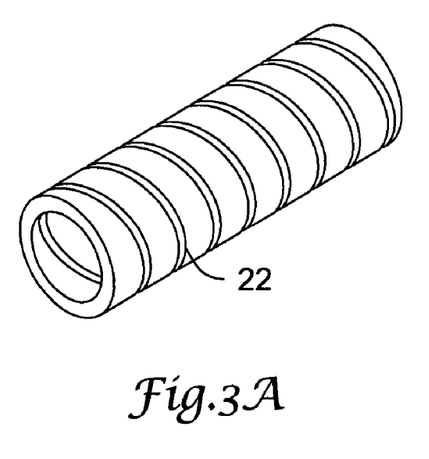
FIG. 3A is a plan view of an alternative reinforcing member for a guidewire in accordance with the invention.
Figure 3B:
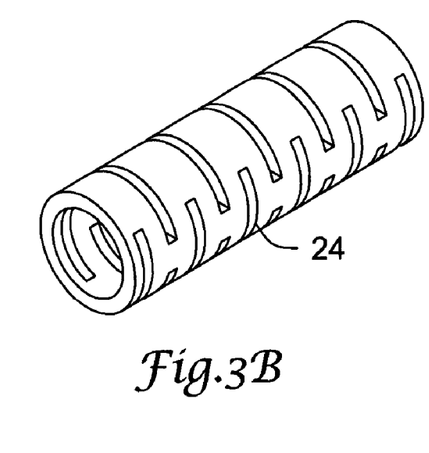
FIG. 3B is a plan view of an alternative reinforcing member for a guidewire in accordance with the invention.

As more clearly shown in FIGS. 3A and 3B, tubular segment 20 may include at least one groove or cut 24. The groove or cut 24 may enhance the properties, such as flexibility, of the tubular segment 20. The groove or cut 24 may extend through substantially the entire thickness of the tube, or the groove or cut 24 may extend only partially through the thickness of the tube (such as a score line). As shown in FIG. 3A, a plurality of grooves or cuts 24 may be used to acquire the necessary flexibility. As shown in FIG. 3B, the groove or cut 22 may be helically formed along the length of the tubular segment 20 or a portion thereof. The helical groove or cut 22 may extend only partially through the thickness of the tube (such as a score line) or may extend through substantially the entire thickness of the tube. The pitch of the helical groove or cut 22 may be selected in order to provide desired functionality, or the pitch may vary along the length of the tubular segment 20. The tubular segment 20 may include one or more additional helical grooves or cuts 22 or a combination of grooves or cuts 24 and helical grooves or cuts 22. It is understood that the width and depth of the groove or cut 22, 24 may be of a wide range as may be necessary to attain the desired properties of the tubular segment 20. The groove or cut 22, 24 may be made by any of a variety of techniques known in the art, such as a laser cutter or a plasma cutter.

In some embodiments, an outer member is disposed about at least a portion of the distal section 15 of the core member 14. The outer member may extend from the distal end 17 of guidewire 10 to a point proximal of the distal end 17. The outer member may extend over at least a portion of the reinforcing member, preferably extending substantially over the entire reinforcing member. The outer member may have an outer diameter substantially the same as the diameter of the proximal section 11 of core wire 14, or the outer diameter of the outer member may be larger or smaller than that of the adjacent portion of the core wire 14.

As shown in FIG. 2, the outer member may be a coil 30. The coil 30 may be disposed about the distal section 15 of the guidewire 10. The coil 30 can be formed of a variety of materials including metals, metal alloys, polymers, and the like. Some examples of materials for use in the coil 30 include stainless steel, nickel-chromium alloy, nickel-chromium-iron alloy, cobalt alloy, or other suitable materials. Some additional examples of suitable materials include straightened super elastic or linear elastic alloy (e.g., nickel-titanium) wire, or alternatively, a polymer material, such as a high performance polymer. In some embodiments, the coil 30 or portions thereof can be made of, include or be coated with a radiopaque material such as gold, platinum, tungsten, or the like, or alloys thereof.

The coil 30 can be formed of round or flat ribbon ranging in dimensions to achieve the desired flexibility. In some embodiments, the coil 30 can be a round ribbon in the range of about 0.001 inches to about 0.015 inches in diameter, and can have a length in the range of about 0.1 to about 20 inches. However, other dimensions are contemplated.

The coil 30 can be wrapped in a helical fashion by conventional winding techniques. The pitch of adjacent turns of the coil 30 may be tightly wrapped so that each turn touches the succeeding turn or the pitch may be set such that the coil 30 is wrapped in an open fashion.

A distal tip 32 may be positioned at the distal end 17 of guidewire 10. The distal tip 32 may be a solder, polymer, or other material known in the art. The distal tip 32 may include a radiopaque material, making the location of the distal tip within a body region more visible when using certain imaging techniques, for example, fluoroscopy techniques. Any suitable radiopaque material known in the art can be used. Some examples include precious metals, tungsten, barium subcarbonate powder, and the like, and mixtures thereof. The distal tip 32 may be located distal of coil 30. The distal tip, or a portion thereof, may be located within the distal portion of coil 30.

Figure 2A:
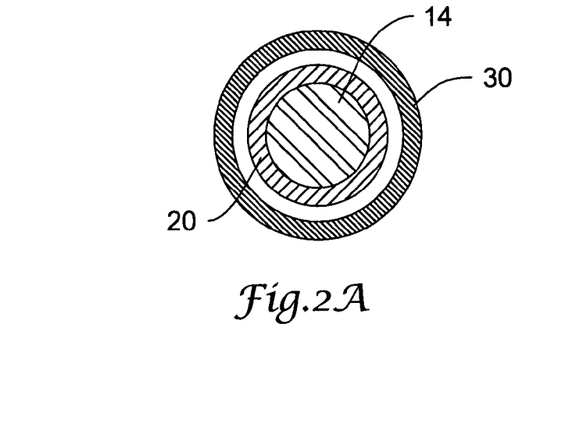
FIG. 2A is an orthogonal cross-sectional view of the guidewire in FIG. 2.
Figure 4:
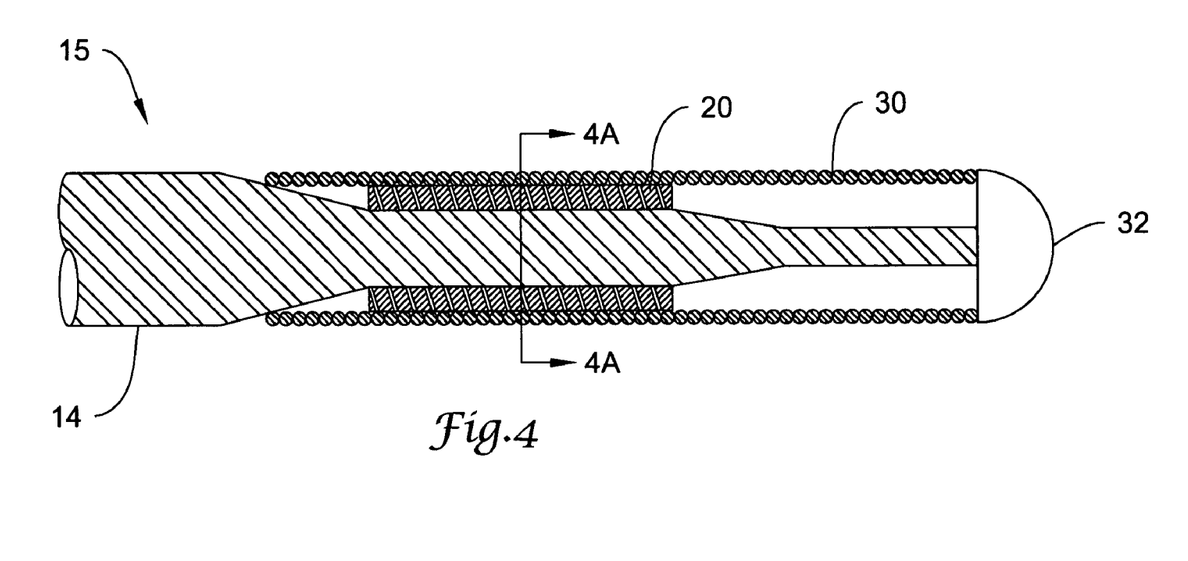
FIG. 4 is a partial cross-sectional view of a variation of the distal portion of a guidewire.
Figure 4A:
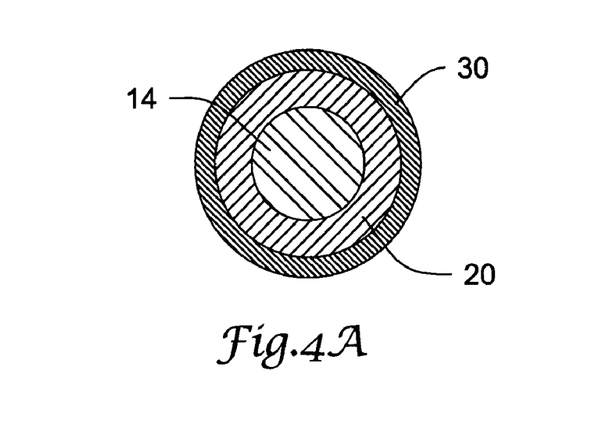
FIG. 4A is an orthogonal cross-sectional view of the guidewire in FIG. 4.

A variation of the distal section 15 of guidewire 10 is shown in FIG. 4. The distal section 15 of guidewire 10 is substantially the same as in FIG. 2, except for the relative spacing between the tubular segment 20 and the coil 30. As best shown in FIG. 4A, the tubular segment 20 is located adjacent to the coil 30, whereas in FIG. 2A, there is a space between the tubular segment 20 and the coil 30. The relative spacing between the tubular segment 20 and the coil 30 may provide unique characteristics of the distal section 15 that may be desirable during a procedure.

Figure 5:
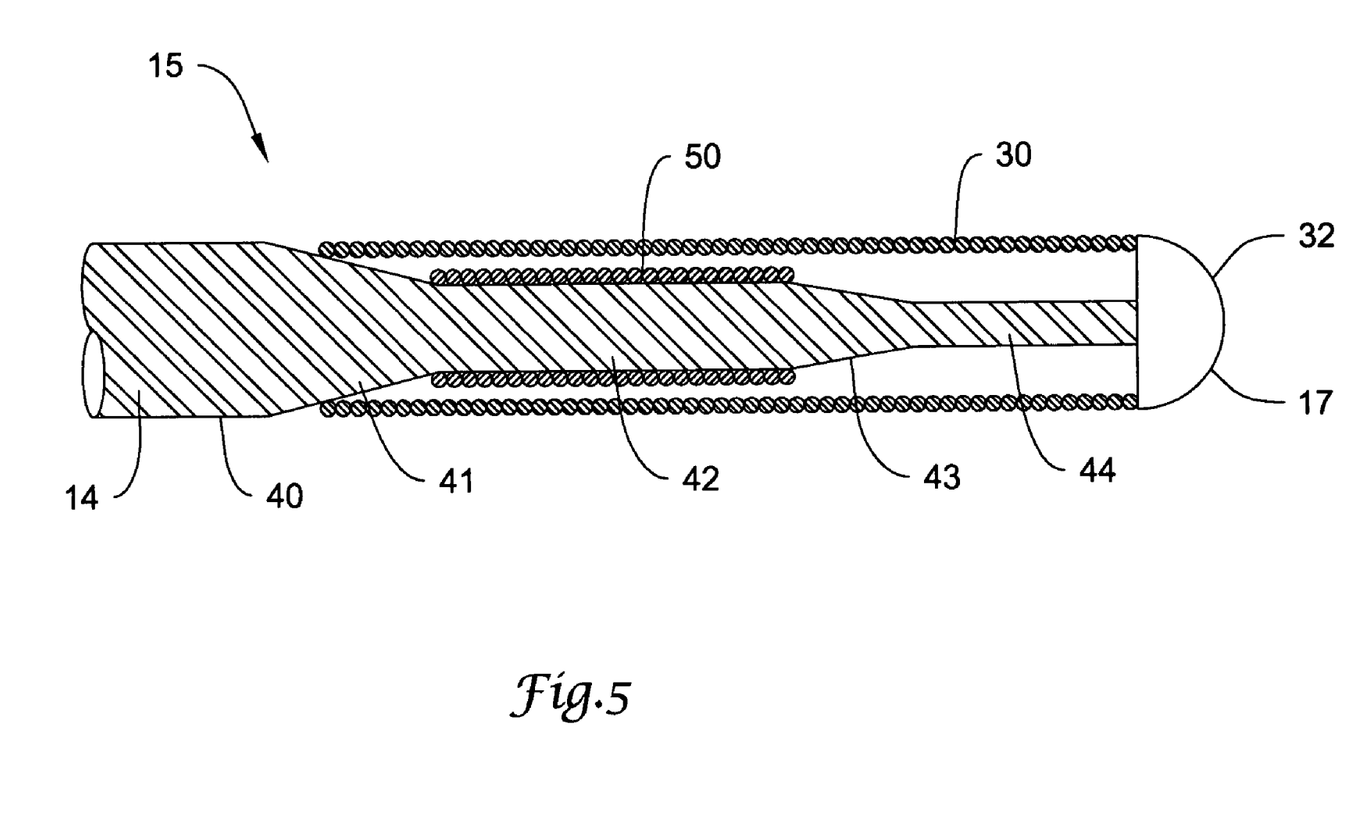
FIG. 5 is a partial cross-sectional view of another embodiment of the distal portion of a guidewire.

An alternative embodiment of the distal section 15 of the guidewire 10 is shown in FIG. 5. Core wire 14 includes a proximal portion 40, an intermediate portion 42, and a distal portion 44. A taper 41 is located between proximal portion 40 and intermediate portion 42 in order to transition from a first cross-section in proximal portion 40 to a second cross-section in intermediate portion 42. A taper 43 is located between intermediate portion 42 and distal portion 44 in order to transition from the second cross-section in intermediate portion 42 to a third cross-section in distal portion 44. The tapering and constant cross-sectional area portions as shown in FIG. 4 are not intended to be limiting, and alterations of this arrangement can be made without departing from the spirit of the invention as discussed earlier.

In one preferred embodiment, a reinforcing member 50 is disposed about the intermediate portion 42 of the core wire 14. The reinforcing member may provide desired characteristics in the region of the intermediate portion 42 of the core wire 14 which may be inadequately provided by the material used in that portion of the core wire 14. For example, the core wire may be stainless steel having superior properties of flexibility and steerability. The reinforcing member may be a nickel-titanium alloy providing enhanced pushability and torqueability to the intermediate portion. In some embodiments, the distal portion 44 may be ribbon shaped providing desired flexibility characteristics at the distal end 17 of the guidewire 10. The distal portion 44 may be shape formed prior to a medical procedure to provide a desired curved tip for enhanced navigation through a tortuous vascular system.

The reinforcing member in FIG. 5 is a coil 50. The coil 50 may be disposed about the distal section 15 of the guidewire 10. The coil 50 can be formed from a variety of materials including metals, metal alloys, polymers, and the like. The coil 50 may preferably include nickel-titanium alloy. Some other examples of material for use in the coil 50 include stainless steel, nickel-chromium alloy, nickel-chromium-iron alloy, cobalt alloy, a polymer material such as a high performance polymer, or other suitable materials. In some embodiments, the coil 50 or portions thereof can be made of, include or be coated with a radiopaque material such as gold, platinum, tungsten, or the like, or alloys thereof. In a preferred embodiment, a nickel-titanium alloy coil is used with a stainless steel core 14.

The coil 50 can be formed of wire ranging in dimensions to achieve the desired flexibility. In some embodiments, the wire can be round wire, rectangular wire, or flat ribbon. Wire of other cross-sectional areas is also contemplated in the invention. The coil 50 can be wrapped in a helical fashion by conventional winding techniques. The pitch of adjacent turns of the coil 50 may be tightly wrapped so that each turn touches the succeeding turn or the pitch may be set such that the coil 50 is wrapped in an open fashion.

As can been seen in FIG. 5, the coil 50 may be disposed about the intermediate portion 42 of core wire 14. The coil 50 may end proximal of the distal portion 44 of the core wire 14. The coil 50 may provide desired characteristics in the region of the intermediate portion 42 of the core wire 14 which may be inadequately provided by the core wire 14.

Figure 6:
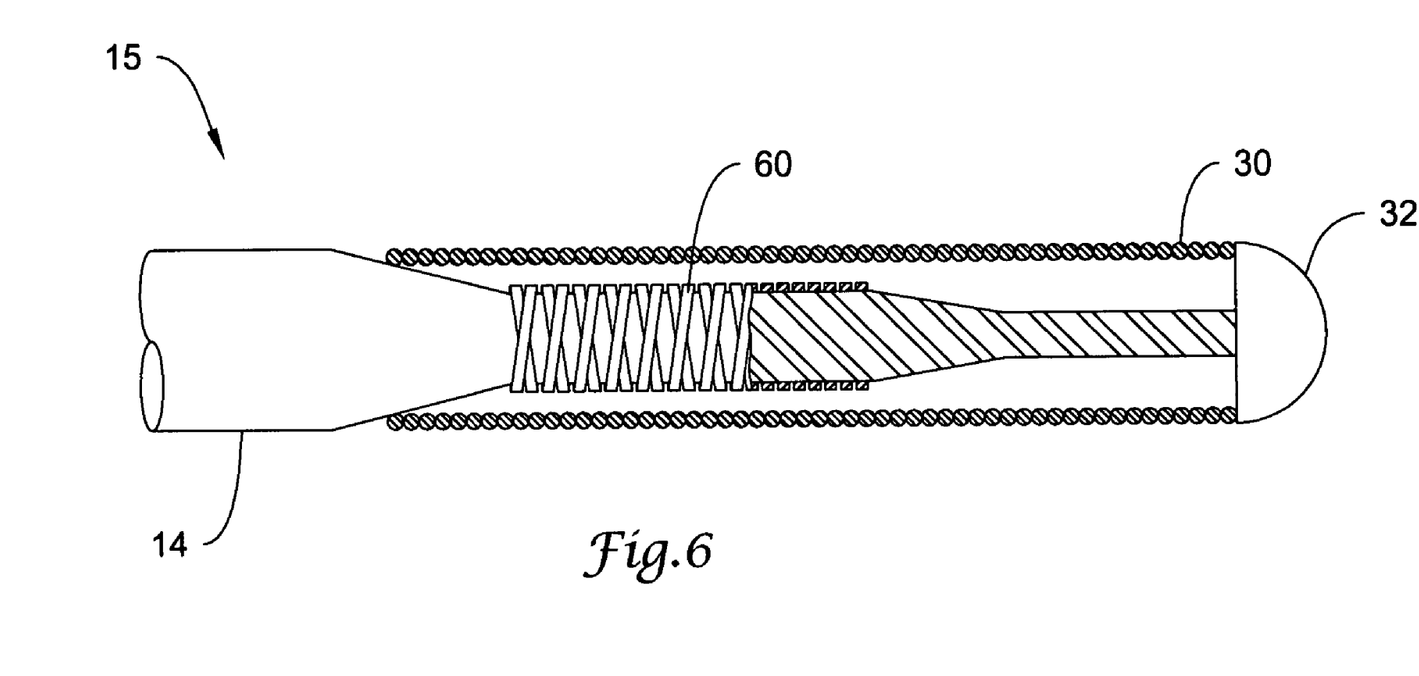
FIG. 6 is a cross-sectional view of an alternative embodiment of the distal portion of a guidewire in accordance with the invention.

FIG. 6 shows an alternative embodiment of the distal section 15 of the guidewire 10. In FIG. 6, the reinforcing member is a helically wrapped wire 60 wound about a portion of the distal section 15 of core wire 14. The helically wrapped wire 60 may be a single strand wound about the core wire 14, or may comprise a plurality of wires 60 wound about the core wire 14. In an embodiment having a plurality of wires 60, such as is shown in FIG. 6, a first strand may be wound in one direction and a second strand wound in an opposing direction. However, wrapping a plurality of wires 60 in the same or similar direction is contemplated within the scope of the invention.

In some embodiments, the helically wrapped wire 60 can be round wire, rectangular wire, or flat ribbon. Wire of other cross-sectional areas is also contemplated in the invention. The helically wrapped wire 60 may be formed from a variety of materials including metals, metal alloys, polymers, fibers, and the like. The wire 60 may preferably include nickel-titanium alloy. Some other examples of material for use in the wire 60 include stainless steel, nickel-chromium alloy, nickel-chromium-iron alloy, cobalt alloy, a polymer material such as a high performance polymer, or other suitable materials. In some embodiments, the wire 60 or portions thereof can be made of, include or be coated with a radiopaque material such as gold, platinum, tungsten, or the like, or alloys thereof. In a preferred embodiment, the helically wrapped wire includes nickel-titanium alloy, and the core contains stainless steel.

In some other embodiments, a polymer jacket tip or combination coil/polymer tip can be used. The polymer jacket tip may extend over at least a portion of the core wire. The outer diameter of the polymer tip may be substantially the same as the diameter of a region of the core wire, or it may be larger or smaller in diameter. A polymer tip having a substantially similar outer diameter may create a smooth transition from a region of the core wire located adjacent to the polymer tip. The smooth transition allows medical devices to be delivered over the guidewire with minimal interference through a transition section, thus increasing efficiency of a medical procedure while reducing the possibility of inadvertent damage to a body region.

Figure 7:
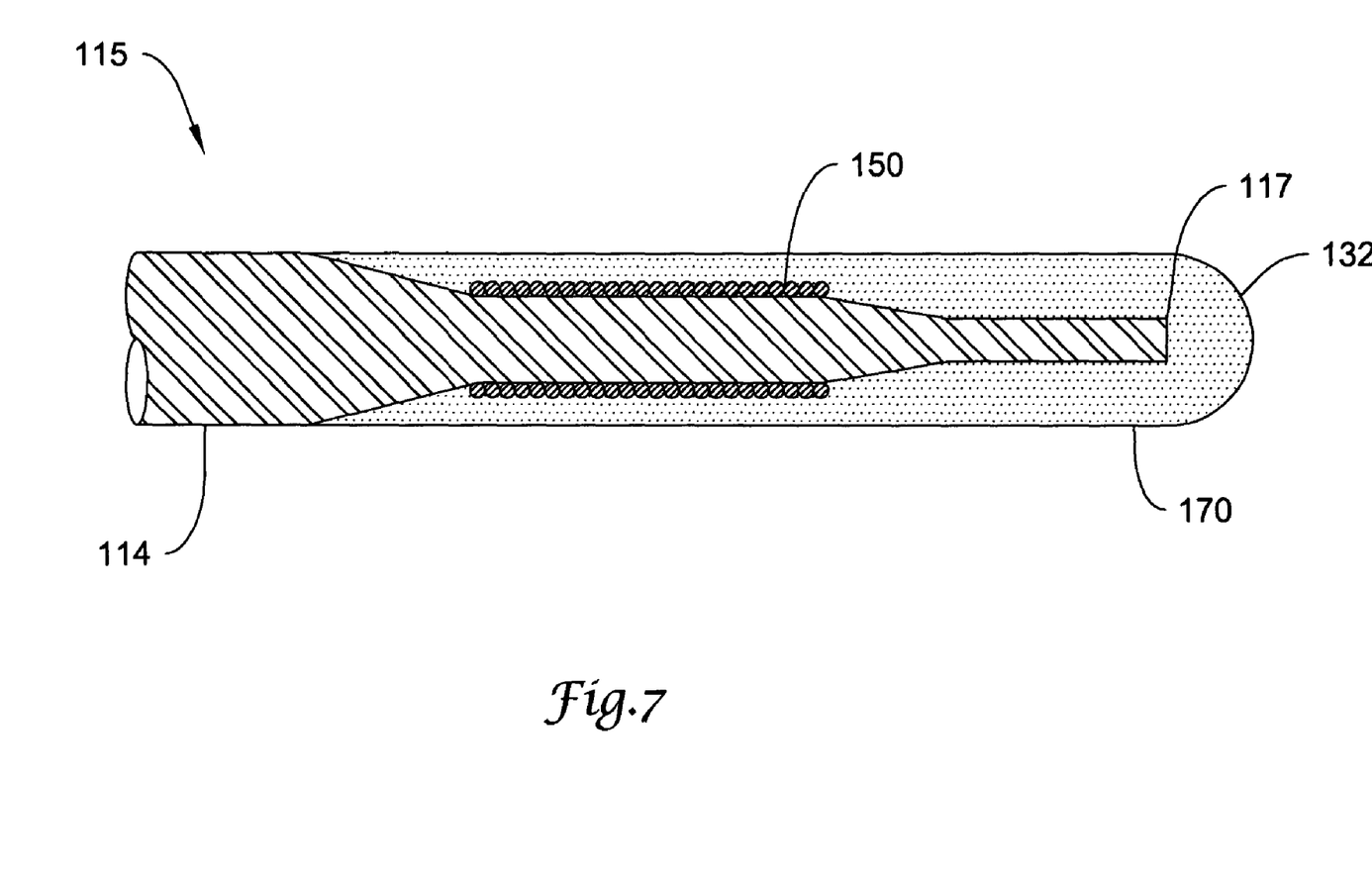
FIG. 7 is a cross-sectional view of a variation of the distal portion of the guidewire in FIG. 6.

For example, in the embodiment shown in FIG. 7, an outer polymer member 170 is disposed over a portion of the core wire 114. In this embodiment, a polymer tip guidewire is formed by including a polymer sheath 170 extending over at least a portion of the distal section 115 of the core wire 114, and forms a rounded tip 132 over the distal end 117 of core member 114. The polymer sheath 170 can be made from any material that can provide the desired strength, flexibility or other desired characteristics. The polymer sheath 170 can, in some non-limiting embodiments, have a length that is in the range of about 1.0 inches to about 25.0 inches, an inner diameter that is in the range of about 0.003 inches to about 0.010 inches and an outer diameter that is in the range of about 0.010 inches to about 0.035 inches.

The use of a polymer can serve several functions, such as improving the flexibility properties of the guidewire assembly. Choice of polymers for the sheath or sleeve 150 will vary the flexibility of the guidewire. For example, polymers with a low durometer or hardness will make a very flexible or floppy tip. Conversely, polymers with a high durometer will make a tip which is stiffer. The use of polymers for the sleeve can also provide a more atraumatic tip for the guidewire. An atraumatic tip is better suited for passing through fragile body passages. Finally, a polymer can act as a binder for radiopaque materials, as discussed in more detail below.

Some suitable materials include polymers, and like material. Examples of suitable polymer material include any of a broad variety of polymers generally known for use as guidewire polymer sleeves. In some embodiments, the polymer material used is a thermoplastic polymer material. Some examples of some suitable materials include polyurethane, elastomeric polyamides, block polyamide/ethers (such as PEBAX™), silicones, and co-polymers. The sleeve may be a single polymer, multiple layers, or a blend of polymers. By employing careful selection of materials and processing techniques, thermoplastic, solvent soluble and thermosetting variants of these materials can be employed to achieve the desired results.

Further examples of suitable polymeric materials include but are not limited to poly(L-lactide) (PLLA), poly(D,L-lactide) (PLA), polyglycolide (PGA), poly(L-lactide-co-D, L-lactide) (PLLA/PLA), poly(L-lactide-co-glycolide) (PLLA/PGA), poly(D, L-lactide-co-glycolide) (PLA/PGA), poly(glycolide-co-trimethylene carbonate) (PGA/PTMC), polyethylene oxide (PEO), polydioxanone (PDS), polycaprolactone (PCL), polyhydroxylbutyrate (PHBT), poly(phosphazene), poly D,L-lactide-co-caprolactone) (PLA/PCL), poly(glycolide-co-caprolactone) (PGA/PCL), polyanhydrides (PAN), poly(ortho esters), poly(phosphate ester), poly (amino acid), poly(hydroxy butyrate), polyacrylate, polyacrylamid, poly(hydroxyethyl methacrylate), polyurethane, polysiloxane and their copolymers.

In some embodiments, the sheath 170 or portions thereof can include or be doped with radiopaque material to make the sheath 170 or portions thereof more visible when using certain imaging techniques, for example fluoroscopy techniques. Any suitable radiopaque material known in the art can be used. Some examples include precious metals, tungsten, barium subcarbonate powder, and the like, and mixtures thereof. In some embodiments, the polymer can include different sections having different amounts of loading with radiopaque material. For example, the sheath or sleeve 150 can include a distal section having a higher level of radiopaque material loading, and a proximal section having a correspondingly lower level of loading.

The sheath 170 can be disposed around and attached to the guidewire assembly 110 using any suitable technique for the particular material used. In some embodiments, the sheath 170 can be attached by heating a sleeve of polymer material to a temperature until it is reformed around the guidewire assembly 110. In some embodiments, the sheath 170 can be attached using heat-shrinking techniques. In other embodiments, the sheath or sleeve 170 can be co-extruded with the core wire 114. The sheath 170 can be finished, for example, by a centerless grinding or other method to provide the desired diameter and to provide a smooth outer surface.

Figure 8:
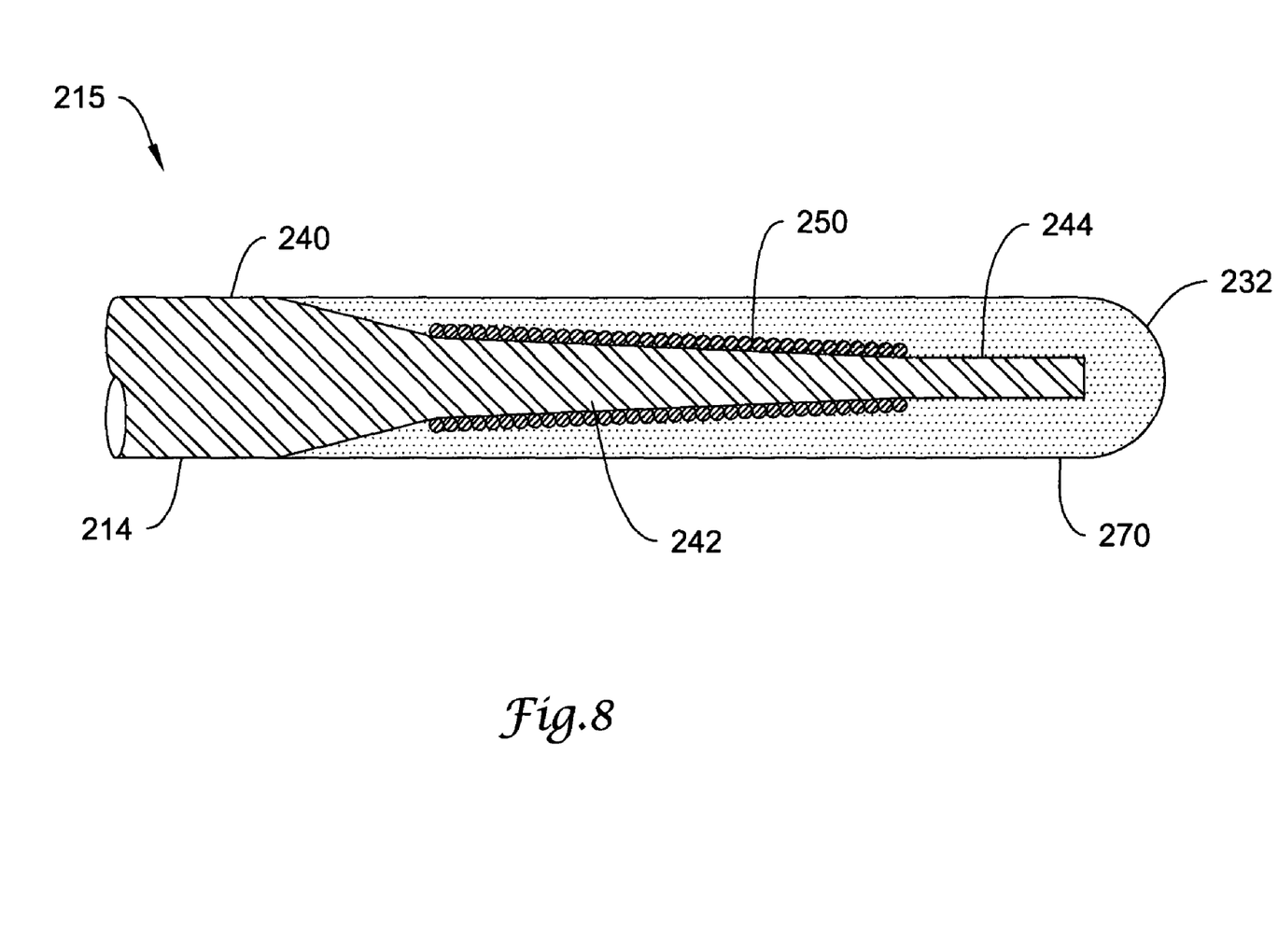
FIG. 8 is a cross-sectional view of a variation of the distal portion of the guidewire in FIG. 6.

FIG. 8 shows an alternative embodiment of a guidewire having a distal section 215. The guidewire includes a reinforcing member 250 disposed on a tapered portion 242 of the core wire 214. It is therefore contemplated that the reinforcing member 250 may be located on a portion of the core wire 214 having a variable cross-section. The tapered portion 242 is located between proximal region 240 and distal region 244. Distal region 244 may be of a circular cross-section or may be ribbon shaped. Outer polymer layer 270 may be disposed over at least a portion of the distal region 215 forming a rounded tip 232. Alternatively, a coil could overlay the reinforcing member 250, as in FIG. 2.

Figure 9:
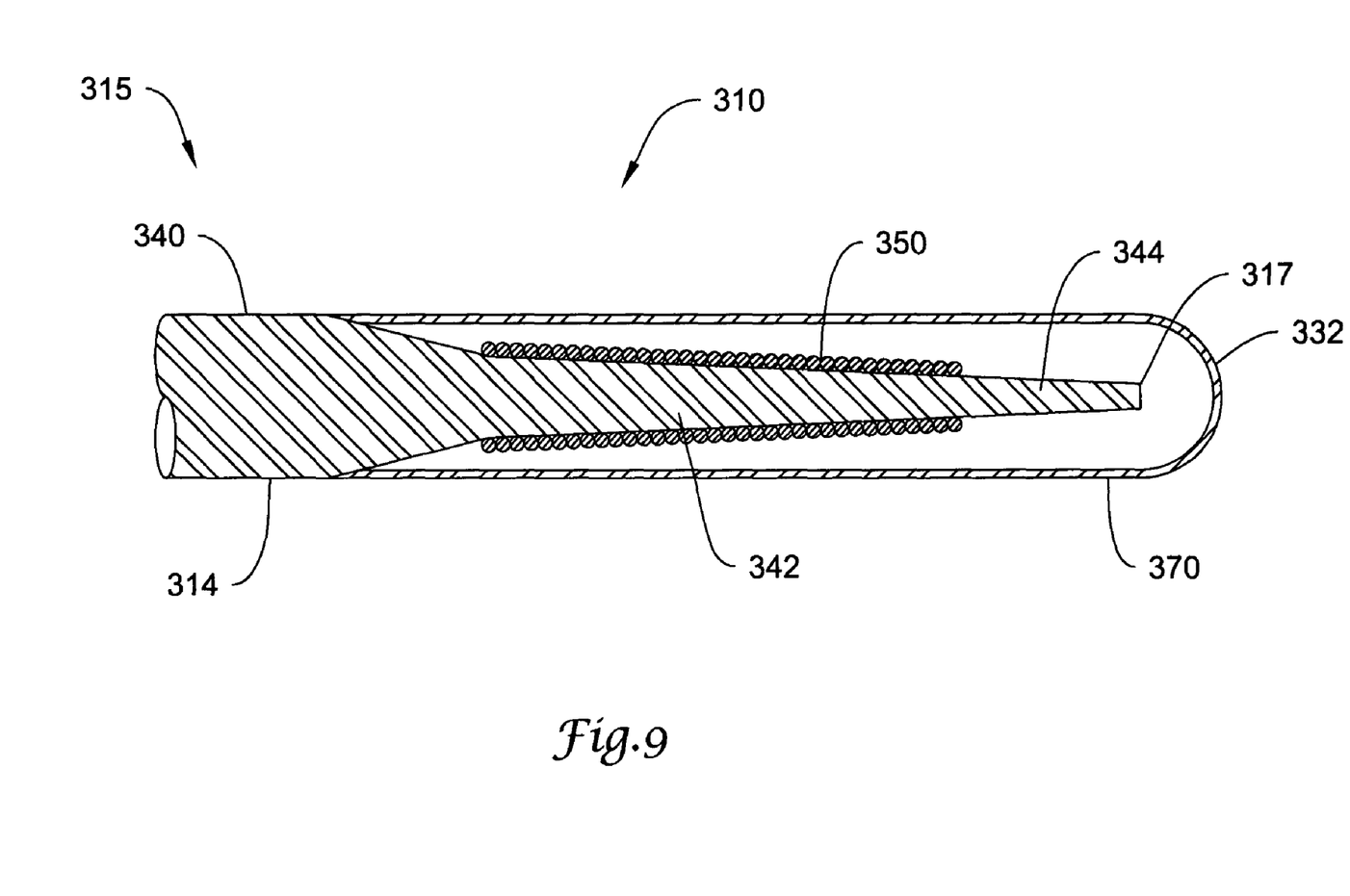
FIG. 9 is a cross-sectional view of an alternative embodiment of the distal portion of a guidewire in accordance with the invention.

FIG. 9 shows an alternative embodiment of a distal region 315 of a guidewire. The guidewire includes a core wire 314 having a continuous taper from a proximal tapered portion 342, through a distal tapered portion 344, to the distal end 317 of the core wire 314. A reinforcing member 350 is disposed on at least a portion of the tapered portion 342, 344. An outer polymer member 370 extends over at least a portion of the tapered portion 342, 344, and preferably extends to a proximal portion 340 of the core wire 314.

Figure 10:
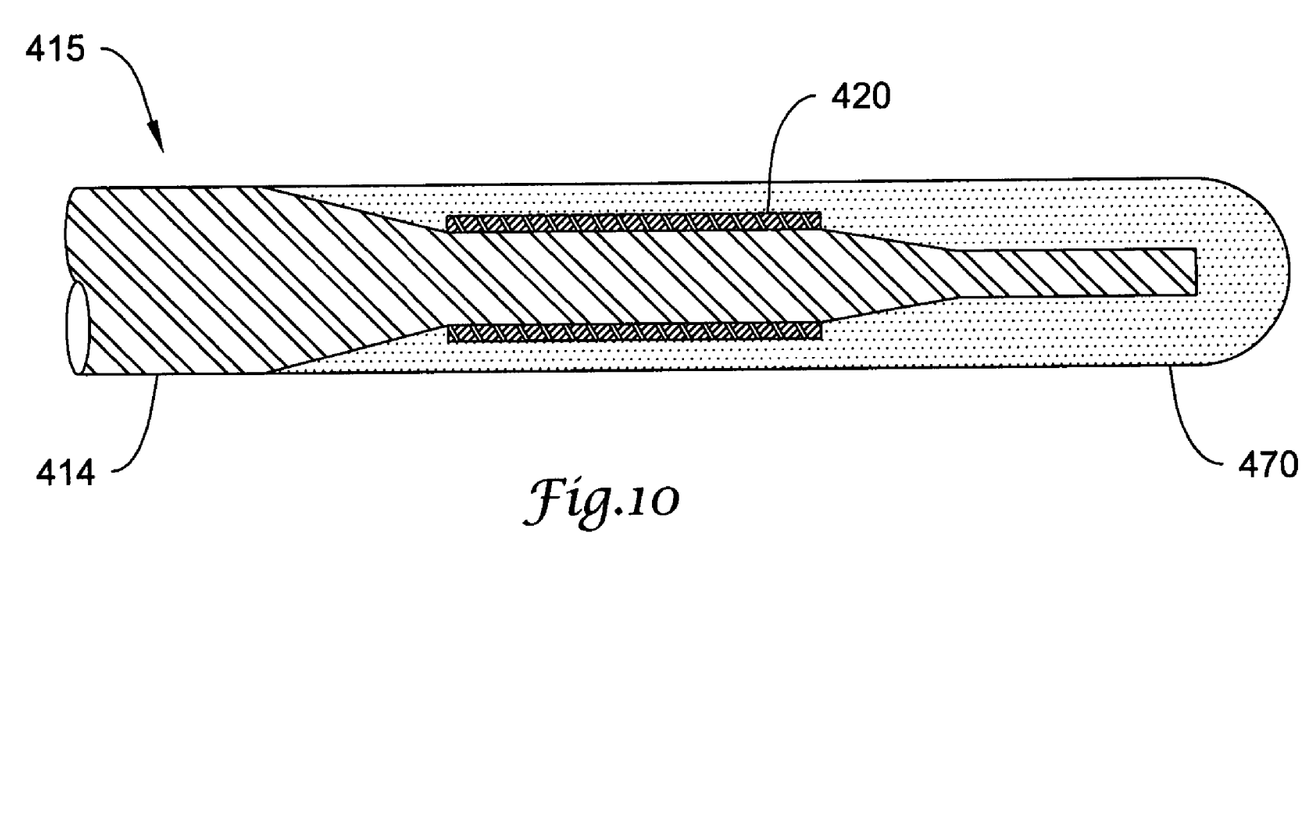
FIG. 10 is a partial cross-sectional view of another embodiment of the distal portion of a guidewire.

Other embodiments of the invention incorporate similar elements of the invention in additional configurations. Additional figures have been included to further describe the invention. However, selected embodiments depicted in the drawings are not intended to limit the scope of the invention For example, FIG. 10 combines a reinforcing member comprising a tubular member 420 like that of FIG. 2 with a polymer sleeve 470 like that in FIG. 7. The tubular member 420 is disposed on a distal portion 415 of the core wire 414. The tubular member 420 may have cuts, grooves, or similar features as disclosed with tubular member 20.

Figure 11:
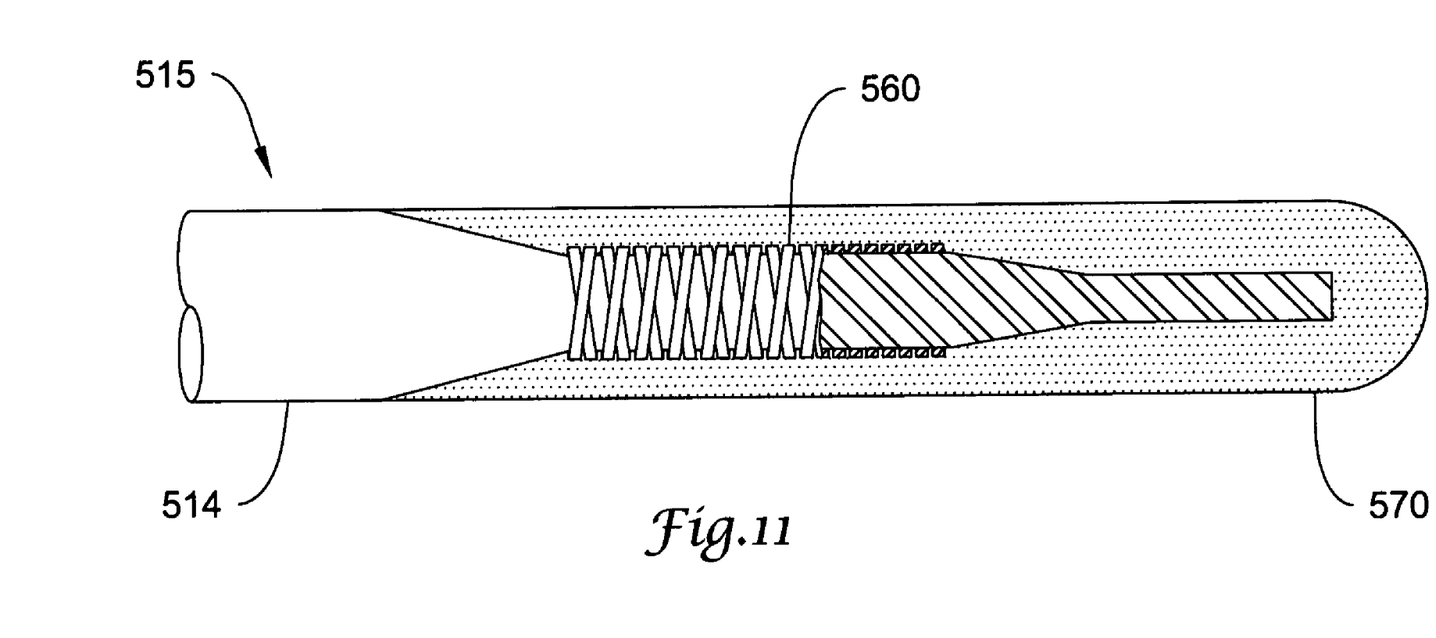
FIG. 11 is a partial cross-sectional view of an alternative embodiment of a guidewire in accordance with the invention.

FIG. 11 depicts an additional embodiment in accordance with the invention. Helically wrapped wire 560 is disposed along at least a portion of the distal region 515 of core wire 514. As in FIG. 5, helically wrapped wire 560 may be a single strand or a plurality of strands. Additionally, in a preferred embodiment, helically wrapped wire 560 includes a first strand wound about a portion of the core wire 514 and a second strand wound about the portion of the core wire 514 in an opposing direction. Polymer sleeve 570 is positioned over at least a portion of the distal region 515. The polymer sleeve 570 preferably has an outside diameter substantially the same as the diameter of the core wire 514 adjacent the polymer sleeve 570.

Additionally, in some embodiments, a coating, for example a lubricious (e.g., hydrophilic) or other type of coating, may be applied over portions or all of the core wire, reinforcing member, outer member, or other portions of the guidewire. Hydrophobic coatings such as fluoropolymers provide a dry lubricity which improves guidewire handling and device exchanges. Lubricious coatings improve steerability and improve lesion crossing capability. Suitable lubricious polymers are well known in the art and may include hydrophilic polymers such as polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference. In some embodiments, the more distal portion of the guidewire is coated with a hydrophilic polymer as discussed above, and the more proximal portions are coated with a fluoropolymer, such as polytetrafluoroethylene (PTFE).

Additionally, other structures, such as radiopaque markers, safety and/or shaping ribbons (coiled or uncoiled), additional coils or reinforcing members, and the like, may be incorporated into the guidewire construction.

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the instant specification. It should be understood that this disclosure is, in many respects, only illustrative. Changes may be made in details, particularly in matters of shape, size, and arrangement of steps without exceeding the scope of the invention. The scope of the invention is, of course, defined in the language in which the appended claims are expressed.

What is claimed is:

1. A guidewire comprising:
   an elongated inner core member including a proximal section and a distal section, the distal section including a proximal portion and a distal portion;
   an elongated reinforcing member having a proximal end and a distal end and an inner surface extending between the proximal and the distal end, the elongated reinforcing member disposed in a fixed position about the proximal portion of the distal section of the core member such that the distal portion of the distal section of the core member is free of the reinforcing member and such that the inner surface of the elongated reinforcing member is in contact with the proximal portion of the core member along the entire length of the reinforcing member from the proximal end to the distal end of the reinforcing member; and
   an outer coil member having a proximal end and a distal end, the outer coil member disposed about the distal section of the core member, there being no intervening layer of material between the distal portion of the distal section of the inner core member and the outer coil member; and
   the outer coil member is located exterior of the elongated reinforcing member such that there exists an unoccupied space between the entire perimeter of the elongated reinforcing member and the outer coil member;
   wherein the proximal end of the outer coil member is located proximal of the proximal end of the elongated reinforcing member.

2. The guidewire of claim 1, wherein the reinforcing member comprises a nickel-titanium alloy.

3. The guidewire of claim 1, wherein the reinforcing member comprises a nickel-titanium alloy tube having at least one cut or groove defined therein.

4. The guidewire of claim 1, wherein the reinforcing member comprises a nickel-titanium alloy tube having at least one helical cut or groove defined along a length of the reinforcing member.

5. The guidewire of claim 1, wherein the reinforcing member comprises a nickel-titanium alloy coil.

6. The guidewire of claim 1, wherein the reinforcing member comprises at least one nickel-titanium wire helically wrapped about the proximal portion of the distal section.

7. The guidewire of claim 6, wherein the reinforcing member comprises at least a second nickel-titanium wire helically wrapped about the proximal portion of the distal section in an opposing direction.

8. The guidewire of claim 1, wherein the distal portion of the distal section of the core member has a non-circular cross-section.

9. The guidewire of claim 1, wherein the core member comprises stainless steel.

10. The guidewire of claim 1, wherein the outer coil member comprises stainless steel.

11. A guidewire comprising:
   an elongated inner core member, the core member having a proximal region and a distal region with at least a portion of the distal region including stainless steel, the distal region having a proximal section and a distal section;
   an elongated reinforcing member including a nickel-titanium alloy disposed in a fixed position about the inner core member, the reinforcing member having a proximal end and a distal end and a length extending from the proximal end to the distal end, wherein the distal end terminates proximal of the distal section of the distal region of the core member and wherein the reinforcing member contacts the core member along the entire length of the reinforcing member;

wherein the reinforcing member comprises a tube having at least one cut or groove defined therein; and an outer coil member having a proximal end and a distal end, the outer coil member disposed over the distal section of the core member and at least a portion of the reinforcing member; and the outer coil member is located exterior of the elongated reinforcing member such that there exists an unoccupied space between the entire perimeter of the elongated reinforcing member and the outer coil member;

wherein the proximal end of the outer coil member is located proximal of the proximal end of the reinforcing member.

12. The guidewire of claim 11, wherein the distal region of the core member is stainless steel.

13. The guidewire of claim 11, wherein the proximal region of the core member has a diameter and the outer member has an outside diameter substantially equal to the diameter of the proximal region of the core member.

14. The guidewire of claim 11, wherein the outer coil member comprises stainless steel.

15. The guidewire of claim 11, wherein the at least one cut or groove is a helical cut or groove defined along the length of the reinforcing member.

16. A guidewire comprising:

an elongated inner core member including stainless steel, the inner core member including a proximal portion having a first cross-sectional area, an intermediate portion having a second cross-sectional area, wherein the second cross-sectional area is less than the first cross-sectional area, and a distal portion having a ribbon profile;

an elongated tubular member including a nickel-titanium alloy, the tubular member having a proximal end and a distal end and a length extending from the proximal end to the distal end, the tubular member being disposed in a fixed position about the intermediate portion of the inner core member and in contact with the intermediate portion along the entire length of the tubular member;

wherein the reinforcing member comprises a tube having at least one cut or groove defined therein; and a coil tip including stainless steel, the coil tip having a proximal end and a distal end, the coil tip extending over the distal portion of the inner core member and the tubular member;

the coil tip is located exterior of the elongated tubular member such that there exists an unoccupied space between the entire perimeter of the elongated tubular member and the coil tip;

wherein the proximal end of the coil tip is located proximal of the proximal end of the tubular member; and the coil tip has an outside diameter, wherein the outside diameter of the coil tip is substantially equal to the diameter of the proximal portion of the core member to create a smooth transition from the core member to the coil tip.

17. The guidewire of claim 16, wherein at least a portion of the intermediate portion and the distal portion of the core member includes stainless steel.

18. The guidewire of claim 16, wherein the proximal portion of the core member has a diameter and the intermediate portion has a diameter less than the diameter of the proximal portion.

19. The guidewire of claim 16, wherein the at least one cut or groove is a helical cut or groove defined along a length of the tubular member.

20. The guidewire of claim 16, wherein the tubular member includes a plurality of cuts formed therein.

* * * * *